United States Patent [19]

Scalone et al.

[11] Patent Number: 5,534,635
[45] Date of Patent: Jul. 9, 1996

[54] PROCESS FOR PREPARING PYRIDINE-2-CARBOXAMIDES

[75] Inventors: Michelangelo Scalone; Peter Vogt, both of Birsfelden, Switzerland

[73] Assignee: Hoffmann-La Roche Inc., Nutley, N.J.

[21] Appl. No.: 304,460

[22] Filed: Sep. 12, 1994

Related U.S. Application Data

[62] Division of Ser. No. 67,329, May 25, 1993, Pat. No. 5,380,861, which is a continuation of Ser. No. 740,692, Aug. 6, 1991, abandoned, which is a continuation of Ser. No. 484,292, Feb. 26, 1990, abandoned.

[30] Foreign Application Priority Data

Feb. 28, 1989 [CH] Switzerland ............................ 736/89
Dec. 4, 1989 [CH] Switzerland ............................ 4323/89

[51] Int. Cl.⁶ .................... C07D 213/81; C07D 213/56
[52] U.S. Cl. .................... 546/323; 546/318; 546/327
[58] Field of Search ............................................. 546/323

[56] References Cited

U.S. PATENT DOCUMENTS

| | | | |
|---|---|---|---|
| 2,749,350 | 6/1956 | Nowlin | 546/318 |
| 3,862,159 | 1/1975 | Umezawa et al. | 546/326 |
| 4,764,522 | 8/1988 | Imhof et al. | 514/354 |

FOREIGN PATENT DOCUMENTS

| | | |
|---|---|---|
| 0283194 | 9/1988 | European Pat. Off. . |
| 2163746 | 3/1986 | United Kingdom . |

OTHER PUBLICATIONS

Tilley, et al., J. Org. Chem. 53,386 (1988).
Sakamoto, et al., Chem. Pharm. Bull. 36,1890 (1988).
Sonogashira, et al., Tetrahedron Letters, 50, 4467 (1975).
Lee, et al., J. Org. Chem. 44, 2726 (1979).
Chem. Abstrs. vol. 95(9) Abstr. No. 80892-S Aug. 31, 1981.
Chem. Abstrs. vol. 99(7) Abstr. No. 53 823-W Aug. 15, 1983.
Chem. Abstr. vol. 73(25) Abstr. No. 130 851-W, Dec. 21, 1970.
Chem. Abstr. vol. 105(11) Abstr. No. 97 323e, Sep. 15, 1986.
Chem. Abstr. vol. 109(25) Abstr. No. 231 063h, Dec. 19, 1988.

R. F. Heck, Palladium Reagents In Organic Synthesis, Academic Press (1985) pp. 299–306, 348–362.
Sakamoto, et al., Palladium (o)–Catalyzed Condensation of Bromopyridines With α–Substituted Acetonitriles, Heterocycles, 27(6) 1353 (1988).

Primary Examiner—Alan L. Rotman
Attorney, Agent, or Firm—George M. Gould; George W. Johnston; Ellen Ciambrone Coletti

[57] ABSTRACT

It has been found that pyridine-2-carboxamides of the formula

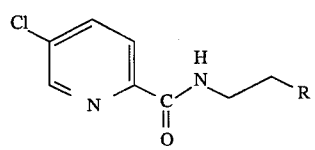

I wherein R is amino or a residue convertible into amino, and pharmaceutically usable acid addition salts of that carboxamide in which R is amino can be prepared in a simple manner and in good yield by reacting 2,5-dichloropyridine in the presence of a palladium-phosphine catalyst with an alkyne of the formula $R^1$—C≡CH   III wherein $R^1$ is hydrogen, lower-alkyl, trimethylsilyl or the group —$(R^2)(R^3)$—COH and $R^2$ and $R^3$ each independently are hydrogen or lower-alkyl or together are cyclopentyl or cyclohexyl,
oxidizing the resulting alkyne to give 5-chloropyridine-2-carboxylic acid and reacting this acid or a reactive functional derivative thereof with an amino compound of the formula
or with carbon monoxide and an amino compound of formula VI or with carbon monoxide and a lower alkanol which is optionally mixed with water and reacting the resulting acid or the resulting ester with an amino compound of formula VI. The compound of formula I in which R is amino is a known compound which is a reversible and highly active MAO-B inhibitor.

20 Claims, No Drawings

PROCESS FOR PREPARING PYRIDINE-2-CARBOXAMIDES

This is a division of application Ser. No. 08/067,329 filed May 25, 1993 now U.S. Pat. No. 5,385,861, which is a Continuation of Ser. No. 07/740,692, filed Aug. 6, 1991 abandoned, which is a Continuation of Ser. No. 07/484,292, field Feb. 26, 1990, now abandoned.

BRIEF SUMMARY OF THE INVENTION

The present invention relates to a process for the preparation of pyridine-2-carboxamides of the formula

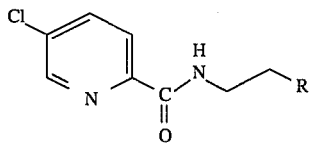

wherein R is amino or a residue convertible into amino, and of pharmaceutically usable acid addition salts of that compound in which R is amino.

The compounds of formula I above in which R is a residue convertible into amino are valuable intermediates and can be used, for example, for the manufacture of N-(2-aminoethyl)-5-chloropyridine-2-carboxamide, i.e. the compound of formula I in which R is amino. This compound as well as its pharmaceutically usable acid addition salts have a pronounced, reversible and highly selective monoamine oxidase B (MAO-B) inhibiting property and are accordingly suitable for the treatment of depressive states, Parkinsonism and cognitive disorders.

The process in accordance with the invention comprises reacting 2,5-dichloropyridine of the formula

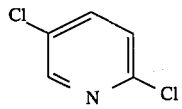

in the presence of a palladium-phosphine catalyst (a) with an alkyne of the formula

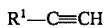

wherein $R^1$ is hydrogen, lower-alkyl, trimethylsilyl or the group —$(R^2)(R^3)$—COH and $R^2$ and $R^3$ each independently are hydrogen or lower-alkyl or together are cyclopentyl or cyclohexyl,
oxidizing the resulting alkyne of the formula

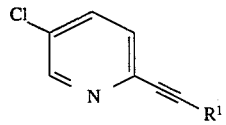

wherein $R^1$ is as described above,
to give 5-chloropyridine-2-carboxylic acid of the formula

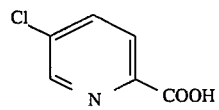

and reacting this or a reactive functional derivative thereof with an amino compound of the formula

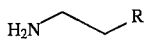

wherein R is as described above, or b) with carbon monoxide and an amino compound of formula VI above or with carbon monoxide and a lower alkanol optionally mixed with water to give 5-chloropyridine-2-carboxylic acid of formula V above or a lower alkyl ester thereof and reacting the resulting acid or the resulting lower alkyl ester or another reactive functional derivative of this acid with an amino compound of formula VI above, c) where the compound of formula I in which R is amino is desired, if necessary converting into amino the residue R in a resulting compound of formula I in which R is a residue convertible into amino, and d) if desired converting the resulting compound into a pharmaceutically usable acid addition salt.

DETAILED DESCRIPTION OF THE INVENTION

The invention is related to a novel process for the preparation of pyridine-2-carboxamides of the formula

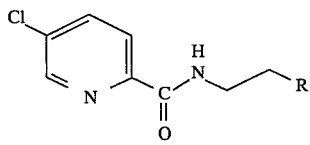

wherein R is amino or a residue convertible into amino, and of pharmaceutically usable acid addition salts of that compound in which R is amino.

The compounds of formula I above wherein R is a residue convertible into amino are valuable intermediates and can be used, for example, for the preparation of N-(2-aminoethyl)-5-chloropyridine-2-carboxamide, i.e. the compound of formula I wherein R is amino. This compound as well as its pharmaceutically usable acid addition salts have a pronounced, reversible and highly selective monoamine oxidase B (MAO-B) inhibiting property and are accordingly suitable for the treatment of depressive states, Parkinsonism and cognitive disorders. A process for the preparation of N-(2-aminoethyl)-5-chloropyridine-2-carboxamide and its pharmaceutically usable salts—inter alia from compounds of formula I above in which R is a residue convertible into amino—as well as their interesting pharmacological properties are described, for example, in British Patent Specification No. 2163746.

As used herein, the term "lower-alkyl" denotes straight-chain and branched hydrocarbon residues with 1–7, preferably 1–4, carbon atoms such as methyl, ethyl, propyl, isopropyl, butyl, isobutyl, sec.-butyl, t-butyl, pentyl, hexyl, heptyl and the like. Similarly, the terms "$C_{1-8}$-alkyl" and "$C_{1-4}$-alkyl" denote corresponding hydrocarbon residues with 1–8 and, respectively, 1–4 carbon atoms. As used herein, the term "$C_{1-4}$-alkoxy" denotes alkyl ether groups wherein "$C_{1-4}$-alkyl" is as described above. As used herein, the term "halogen" denotes the four halogens fluorine, chlorine, bromine and iodine.

The process in accordance with the invention comprises reacting 2,5-dichloropyridine of the formula

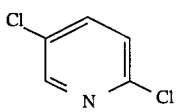

in the presence of a palladium-phosphine catalyst (a) with an alkyne of the formula

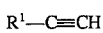

wherein $R^1$ is hydrogen, lower-alkyl, trimethylsilyl or the group $-(R^2)(R^3)-COH$ and $R^2$ and $R^3$ each independently are hydrogen or lower-alkyl or together are cyclopentyl or cyclohexyl, oxidizing the resulting alkyne of the formula

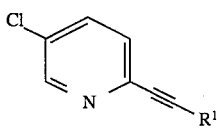

wherein $R^1$ is as described above, to give 5-chloropyridine-2-carboxylic acid of the formula

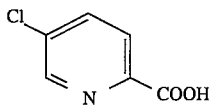

and reacting this or a reactive functional derivative thereof with an amino compound of the formula

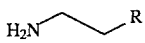

wherein R is as described above, or b) with carbon monoxide and an amino compound of formula VI above or with carbon monoxide and a lower alkanol optionally mixed with water to give 5-chloropyridine-2-carboxylic acid of formula V above or a lower alkyl ester thereof and reacting the resulting acid or the resulting lower alkyl ester or another reactive functional derivative of this acid with an amino compound of formula VI above, c) where the compound of formula I wherein R is amino is desired, if necessary converting into amino the residue R in a resulting compound of formula I in which R is a residue convertible into amino, and d) if desired converting the resulting compound into a pharmaceutically usable acid addition salt.

The alkynylation of 2,5-dichloropyridine of formula II with an alkyne of formula III in the presence of a palladium-phosphine catalyst can be carried out in a manner known per se. Thus, the reaction can be carried out e.g. under anhydrous and oxygen-free conditions in an inert gas atmosphere in the presence of a base and a catalytic amount of copper-(I) iodide in a solvent or solvent mixture which is inert under the reaction conditions at a temperature between about 40° and 150° C., preferably between about 60° and 100° C. Suitable bases are organic bases such as secondary or tertiary amines, e.g. dialkylamines or trialkylamines such as dimethylamine, diethylamine, methylethylamine, trimethylamine, triethylamine, ethyldiisopropylamine and the like, and inorganic bases such as sodium hydroxide or potassium hydroxide, calcium carbonate and the like, whereby excess amine can also serve as the solvent. If the reaction is carried out in the presence of an inorganic base, the use of a phase transfer catalyst or of a crown ether can be of advantage. Diethylamine is the preferred base. Solvents which can be used include aliphatic and aromatic hydrocarbons such as hexane, benzene, toluene, xylene and the like, halogenated aliphatic and aromatic hydrocarbons such as methylene chloride, chlorobenzene and the like, ethers such as diethyl ether, tetrahydrofuran, dioxan and the like, ketones such as acetone, methyl propyl ketone and the like, carboxylic acid esters such as methyl acetate, ethyl acetate and the like, alcohols such as t-butanol and the like, dimethylformamide, dimethyl sulphoxide and the like. The pressure is not critical in the reaction in accordance with the invention and therefore the reaction can be carried out at atmospheric pressure or elevated pressures, preferably at atmospheric pressure.

The catalyst is a palladium-phosphine complex compound which, if desired, can also be formed in situ from a palladium component and a phosphine ligand. Palladium components can include metallic palladium, which is optionally supported on a carrier material such as carbon, or a complex or a salt of O-, 2- or 4-valent palladium such as palladium-dichloro-bis(acetonitrile), palladium-bis(dibenzylideneacetone), palladium chloride, palladium acetate and the like. The amount of palladium component conveniently amounts to 0.2–2.0 mol %, preferably 0.2–0.5 mol %. As phosphine ligands there come into consideration chiral and non-chiral mono- and diphosphorus compounds such as are described in Houben-Weyl, Methoden der organischen Chemie, volume El, page 106 et. seq. Georg Thieme Verlag Stuttgart, 1982, and Aspects Homog. Catal., 4, 145–202 (1981), especially those of the formula

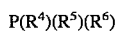

wherein $R^4$, $R^5$ and $R^6$ each independently are $C_{1-8}$-alkyl, cyclohexyl, benzyl, phenyl or phenyl which is substituted by $C_{1-4}$-alkyl, $C_{1-4}$-alkoxy, halogen, trifluoromethyl or phenyl.

The amount of phosphine ligand preferably amounts to 0.01–100 mol per mol of palladium, preferably 0.1–10 mol per mol of palladium. For the in situ preparation of the palladium-phosphine complex compound there is preferably used palladium-dichloro-bis(acetonitrile), palladium-(II) chloride or palladium-(II) acetate.

However, the use of an already formed palladium-phosphine complex compound such as palladium-dichloro-bis-(triphenylphosphine), palladium-tetrakis(triphenylphosphine) and the like is preferred, with palladium-dichloro-bis-(triphenylphosphine) being the preferred complex compound.

The oxidation of a resulting alkyne of formula IV can also be carried out in a manner known per se with permanganate. Thus, the reaction can be carried out in a solvent or solvent mixture which is inert under the reaction conditions at a temperature between about 40° and 120° C., preferably between about 60° and 100° C. Suitable solvents are water and mixtures of water with water-miscible ethers such as tetrahydrofuran, dioxan and the like, ketones such as acetone, methyl ethyl ketone and the like, acetonitrile and the like. The pressure for this reaction step is not critical and therefore the reaction can be carried out at atmospheric pressure or elevated pressures, but preferably at atmospheric pressure.

The reaction of 5-chloropyridine-2-carboxylic acid with an amino compound of formula VI has been described previously, for example in the above-mentioned British Patent Specification No. 2163746.

The amidation of 2,5-dichloropyridine of formula II with carbon monoxide and an amino compound of formula VI in the presence of a palladium-phosphine catalyst can be carried out in a manner known per se. Thus, the reaction can be carried out e.g. under anhydrous and oxygen-free conditions in the presence of a base in a solvent or solvent mixture which is inert under the reaction conditions at a temperature between about 60° and 150° C., preferably between about 100° and 130° C. Suitable bases are organic bases such as tertiary amines, e.g. trialkylamines such as trimethylamine, triethylamine, ethyldiisopropylamine and the like, dialkylarylamines such as N,N-dimethylaniline and the like, triarylamines such as triphenylamine, tritolylamine and the like and inorganic bases such as sodium bicarbonate, potassium bicarbonate, calcium carbonate and the like, whereby excess amine of formula VI can also serve as the base. If the reaction is carried out in the presence of an inorganic base, the use of a phase transfer catalyst or of a crown ether can be of advantage. Triethylamine is the preferred base. Solvents can include aliphatic and aromatic hydrocarbons such as hexane, benzene, toluene, xylene and the like, halogenated aliphatic and aromatic hydrocarbons such as methylene chloride, chlorobenzene and the like, ethers such as diethyl ether, tetrahydrofuran, dioxan and the like, ketones such as acetone, methyl propyl ketone and the like, carboxylic acid esters such as methyl acetate, ethyl acetate and the like, alcohols such as methanol, ethanol, t-butanol and the like, dimethylformamide, dimethyl sulphoxide and the like. The pressure is not critical in the reaction in accordance with the invention and therefore the reaction can be carried out at atmospheric pressure or elevated pressures, preferably at about $10^6$ Pa.

The catalyst is a palladium-phosphine complex compound which is conveniently formed in situ from a palladium component and a phosphine ligand. As palladium components there come into consideration metallic palladium, which is optionally supported on a carrier material such as carbon, or a complex or a salt of O-, 2- or 4-valent palladium such as palladium-bis(dibenzylideneacetone), palladium chloride, palladium acetate and the like. The amount of palladium component can be 0.0001–0.5 mol %, preferably 0.01–0.1 mol %. As phosphine ligands there come into consideration chiral and non-chiral mono- and diphosphorus compounds such as are described in Houben-Weyl, Methoden der organischen Chemie, volume EI, page 106 et. seq. Georg Thieme Verlag Stuttgart, 1982, and. Aspects Homog. Catal., 4, 145–202 (1981), especially those of the formulae $P(R^4)(R^5)(R^6)$ and $(R^4)(R^5)P\text{---}(X)\text{---}P(R^4)(R^5)$ wherein $R^4$, $R^5$ and $R^6$ are as described above and X is binaphthyl or one of the groups —$(CH_2)_n$—, —$CH_2CH_2$—$P(C_6H_5)$—$CH_2CH_2$—,

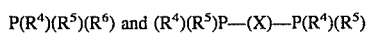

or

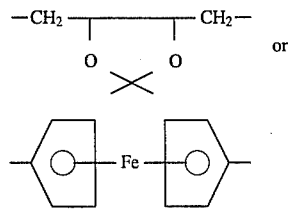

and n is a number of 1–8.

The amount of phosphine ligand can be 0.01–100 mol per mol of palladium, preferably 0.1–10 mol per mol of palladium. For the in situ preparation of the palladium-phosphine complex compound there is preferably used palladium-(II) chloride or palladium-(II) acetate, palladium-dichlorobis(acetonitrile) and a bis(diphenylphosphino)alkane, preferably 1,3-bis(diphenylphosphino)propane.

The conversion of compounds of formula I wherein R is a residue convertible into amino into the compound of formula I wherein R is amino as well as the conversion of the last-mentioned compound into pharmaceutically usable acid addition salts have—as already mentioned above—been described previously, for example in British Patent Specification No. 2163746.

The 2,5-dichloropyridine which is used as the starting material as well as the compounds of formulae III and VI which are used as starting materials are known or can be prepared by known methods.

The following Examples illustrate the present invention in more detail; all temperatures are given in degrees Celsius.

EXAMPLE 1

A 250 ml autoclave is charged under an argon atmosphere with 50 ml of toluene, 5.2 ml (37.2 mmol) of triethylamine, 1.2 mg (0.0067 mmol) of palladium chloride, 5.6 mg (0.0135 mmol) of 1,3-bis(diphenylphosphino)propane, 6.5 g (40.56 mmol) of t-butyl (2-aminoethyl)carbamate and 5.0 g (33.8 mmol) of 2,5-dichloropyridine. After repeated evacuation and pressurization with $10^6$ Pa of nitrogen the autoclave is gassed with $10^6$ Pa of carbon monoxide and heated to 130° while stirring. After heating to 130° for 24 hours the autoclave is cooled, opened and discharged and the orange-brown suspension is filtered through 50 g of silica gel with a 1:1 mixture of toluene and ether as the eluting agent. The fractions containing the desired product (determined by thin-layer chromatography) are combined, evaporated to about 150 ml and stirred vigorously at 70° overnight with a solution of 2 mg of sodium cyanide in 25 ml of water in order to separate the palladium. Thereafter, the organic phase is separated, washed with water and evaporated. Crystallization of the solid residue from toluene/hexane yields 8.51 g (84%) of t-butyl [2-(5-chloropyridine-2-carboxamido)ethyl]carbamate as white crystals, m.p. 106°–108°.

EXAMPLE 2

The amidation of 5 g (33.8 mmol) of 2,5-dichloropyridine in the presence of 475 mg of palladium-dichloro-bis(triphenylphosphine) and 355 mg of triphenylphosphine is carried out in a manner analogous to Example 1. Working-up of the crude product as described in Example 1 yields 8.83 g (87.2%) of pure t-butyl [2-(5-chloropyridine- 2-carboxamido)ethyl]carbamate which is identical with the product obtained in Example 1.

EXAMPLE 3

The amidation of 5 g (33.8 mmol) of 2,5-dichloropyridine in the presence of 2.0 mg of palladium chloride and 4.8 mg of 1,3-bis(diphenylphosphino)propane is carried out at 110° in a manner analogous to Example 1. Working-up of the crude product as described in Example 1 yields 9.45 g (93.3%) of pure t-butyl [2-(5-chloropyridine-2 -carboxamido)ethyl]carbamate which is identical with the product obtained in Example 1.

EXAMPLE 4

The amidation of 5 g (33.8 mmol) of 2,5-dichloropyridine in the presence of 11.4 mg of palladium acetate and 75 mg of 1,3-bis(diphenylphosphino)propane is carried out in a manner analogous to Example 1. Working-up of the crude product as described in Example 1 yields 9.66 g (95.4%) of pure t-butyl [2-(5-chloropyridine-2-carboxamido)ethyl]carbamate which is identical with the product obtained in Example 1.

EXAMPLE 5

The amidation of 5 g (33.8 mmol) of 2,5-dichloropyridine in the presence of 27 mg of bis(palladium)-tris(dibenzylideneacetone)chloroform adduct and 75 mg of 1,3-bis(diphenylphosphino)propane is carried out in a manner analogous to Example 1. Working-up of the crude product as described in Example 1 yields 9.20 g (90.8%) of pure t-butyl [2-(5-chloropyridine-2-carboxamido)ethyl]carbamate which is identical with the product obtained in Example 1.

EXAMPLE 6

1.0 g (6.75 mmol) of 2,5-dichloropyridine are reacted with 2.49 g (15.54 mmol) of t-butyl (2-aminoethyl)carbamate, 197 mg of palladium-bis(dibenzylideneacetone) and 147 mg of 1,3-bis(diphenylphosphino)propane in 10 ml of toluene in a round flask at 120° under a carbon monoxide atmosphere for 2.7 hours. Working-up of the crude product carried out analogously to Example 1 yields 1.7 g (83%) of pure t-butyl [2-(5-chloropyridine-2-carboxamido)ethyl]carbamate which is identical with the product obtained in Example 1.

EXAMPLE 7

The amidation of 5 g (33.8 mmol) of 2,5-dichloropyridine in the presence of 13.5 mg of palladium-dichloro-bis(acetonitrile) and 80 mg of 1,3-bis(diphenylphosphino)propane in 50 ml of tetrahydrofuran is carried out in a manner analogous to Example 1. Working-up of the crude product as described in Example 1 yields 9.15 g (90.3%) of pure t-butyl [2-(5-chloropyridine-2-carboxamido)ethyl]carbamate which is identical with the product obtained in Example 1.

EXAMPLE 8

The amidation of 5 g (33.8 mmol) of 2,5-dichloropyridine in the presence of 13.5 mg of palladium-dichloro-bis(acetonitrile) and 80 mg of 1,3-bis(diphenylphosphino)propane in 50 ml of ethyl acetate is carried out in a manner analogous to Example 1. Working-up of the crude product as described in Example 1 yields 9.51 g (93.9%) of pure t-butyl [2-(5-chloropyridine-2-carboxamido)ethyl]carbamate which is identical with the product obtained in Example 1.

EXAMPLE 9

The amidation of 5 g (33.8 mmol) of 2,5-dichloropyridine in the presence of 137 mg of tetrabutylammonium iodide and 3.12 g of sodium bicarbonate is carried out in a manner analogous to Example 2. Working-up of the crude product as described in Example 1 yields 7.53 g (74.3%) of pure t-butyl [2-(5-chloropyridine-2-carboxamido)ethyl]carbamate which is identical with the product obtained in Example 1.

EXAMPLE 10

The amidation of 5 g (33.8 mmol) of 2,5-dichloropyridine in the presence of 12.1 g (202 mmol) of ethylenediamine, 8.8 mg of palladium-dichloro-bis(acetonitrile) and 21 mg of 1,3-bis(diphenylphosphino)propane is carried out at 110° in a manner analogous to Example 1. After the addition of 1.91 g (35.5 mmol) of sodium methylate and evaporation of the reaction mixture there are obtained, by extraction with 3N hydrochloric acid and subsequent basification of the acidic-aqueous solution, 5.05 g (75%) of N-(2-aminoethyl)-5-chloropyridine-2-carboxamide; content according to HPLC: 98.2 wt. %, content of N,N'-ethylene-bis( 5-chloro-2-pyridinecarboxamide): <1% (GC). Conversion of the free base with hydrogen chloride in methanol into the hydrochloride and crystallization from methanol/ether yields N-(2-aminoethyl)-5-chloropyridine-2-carboxamide hydrochloride as white crystals, m.p. 191°–195°.

EXAMPLE 11

The amidation of 10 g (67.6 mmol) of 2,5-dichloropyridine in the presence of 13.2 g (87.8 mmol) of N-benzylethylenediamine, 11.5 g of palladium chloride and 26.5 mg of 1,3-bis(diphenylphosphino)propane is carried out at 110° in a manner analogous to Example 1. By extraction of the reaction mixture with 1N hydrochloric acid and subsequent basification of the acidic-aqueous solution there is obtained N-[2-(benzylamino)ethyl]-5-chloropyridine-2-carboxamide as a pale yellow oil which, by stirring in hexane, yields 16.61 g (85%) of pure N-[2-(benzylamino)ethyl]-5-chloropyridine-2-carboxamide as pale yellow crystals, m.p. 45°–46°.

EXAMPLE 12

A 10 liter sulphonation flask, equipped with a mechanical stirrer, thermometer, intensive condenser, dropping funnel, gas inlet arrangement and calcium chloride tube, is charged under argon with 1.850 kg (12.5 mol) of 2,5-dichloropyridine, 4.600 l of diethylamine and 1.395 kg (16.25 mol) of 2-methyl-3-butyn-2-ol. To the yellow solution obtained there are added while stirring 1.4 g (7.5 mmol) of copper-(I) iodide as well as 26.3 g (37.5 mmol) of palladium-dichloro-bis(triphenylphosphine). The fine suspension is subsequently heated to reflux (about 70°) and the course of the reaction is followed by thin-layer chromatography and gas chromatography. After 24 hours the reaction mixture is cooled to 20° with an ice bath. The solid (diethylamine hydrochloride) is filtered off and rinsed three times with 700 ml of diethylamine each time. The solid contains neither product nor palladium (<4 ppm) and is discarded. The filtrates are combined and evaporated at 40° under reduced pressure. There are thus obtained 2.905 kg of a dark brown residue which becomes solid at 20°, its purity in accordance with GC (Internal Standard used) amounts to 76.1% (g/g).

950 g of crude alkynol are dissolved in 2.300 l of toluene and this solution is placed in a 5 liter separating funnel. Then, two 3 liter separating funnels are each charged with 500 ml of toluene. Subsequently, three 1 l portions of deionized water are allowed to flow through the three separating funnels, in each case with good intermixing. The aqueous phases are discarded and the organic phases are treated in a 6 liter 4-necked round flask, equipped with a mechanical stirrer and thermometer, with 12 g (0.25 mol) of sodium cyanide, 600 ml of deionized water and 1.2 g of tetrabutylammonium bromide. The 2-phase mixture obtained is stirred vigorously at 25° for 24 hours. Then, the two phases are separated and the aqueous phase is washed with 1 l of toluene. The two organic phases are washed in succession with 2.5 l of deionized water. The organic phases are combined and dried over 250 g of sodium sulphate, and the suspension obtained is filtered. The solid is washed with 250 ml of toluene and the combined filtrates are evaporated at 40° under reduced pressure, whereby there are obtained 921 g of 4-(5-chloro-2-pyridyl)-2-methyl-3-butyn-2-ol as a dark brown oil which crystallizes upon standing. This crude product (crude yield; 115%; GC content about 87%) is used directly in the next step.

450 g (2.0 mol) of alkynol in a 10 liter sulphonation flask, equipped with a mechanical stirrer, thermometer, reflux condenser and gas inlet arrangement, are treated under argon with 7 l of warm, deionized water (70°–80°), whereby a yellow emulsion results upon stirring. Then, 1.043 kg (6.6 mol) of potassium permanganate are added in 50 to 75 g portions in such a manner that the internal temperature amounts to 70° to 80°, duration of the addition: about 2 hours. The course of the reaction is followed by thin-layer chromatography. The reaction mixture is held at about 80° with a hot oil bath (100°) until a complete reaction has been determined. Then, the reaction mixture is filtered while hot and the manganese dioxide is washed six times with 1 l of hot deionized water (about 90°) each time. The filtrate is concentrated to a volume of 7 l at 40° under reduced pressure. Traces of manganese dioxide in the concentrate are removed by filtration over fine paper.

To the filtrate in a 10 liter sulphonation flask, equipped with a mechanical stirrer, thermometer, reflux condenser, pH electrode, dropping funnel and gas inlet arrangement, are slowly added dropwise under argon and while stirring at 20° 365 ml of hydrochloric acid (pure) until pH 3 is attained. After completion of the addition of the hydrochloric acid (about 45 minutes) the suspension is cooled to 4° in an ice bath and stirred for one hour. The solid is subsequently filtered off and washed with 2.100 l of deionized water (ice-cold). The residue is dried at 50° overnight under reduced pressure. There are obtained 289 g (90%) of 5-chloropyridine-2-carboxylic acid as a pale beige powder.

567 g (3.6 mol) of 5-chloropyridine-2-carboxylic acid are mixed with 4.540 l of 2-butanol under argon in a 10 liter 4-necked sulphonation flask, equipped with a mechanical stirrer, thermometer, reflux condenser, dropping funnel with pressure balance and gas inlet arrangement. To the solution obtained there are added while stirring 67 ml of concentrated sulphuric acid and the mixture is subsequently heated to reflux, whereby the course of the reaction is followed by gas chromatography. After 3.5 hours about 4% of acid are still present in the mixture in accordance with GC. The ascending condenser is replaced by a descending condenser and 1 l of 2-butanol is added dropwise within 2.5 hours while simultaneously 2 l of solvent are distilled off from the reaction mixture. 97% of ester and 1.5% of acid are detected in the reaction mixture by GC. After distilling off a further 1.5 l of solvent the reaction mixture is cooled to 25° with an ice bath and treated in a 20 liter stirring vessel with 4 l of toluene and a solution of 303 g of sodium bicarbonate in 4 l of deionized water. A further three 20 liter stirring vessels are each charged with 1 l of toluene and the organic phases are washed in sequence with the aqueous phase from the first stirring vessel as well as three times with 1 l of deionized water each time. The aqueous phases are discarded. The organic phases are combined and dried over 1 kg of sodium sulphate. The drying agent is filtered off and the filtrate is evaporated at 300°–50° under reduced pressure. There are obtained 809 g of brown oil as the crude product. 767 g of crude product are subjected to a distillation in a high vacuum. The main fraction boils at 86°–89°/0.1 Pa. There are obtained in this manner 693 g of pale yellow distillate (94%) of 2-butyl 5-chloropyridine-2-carboxylate which forms an oily solid mass at 25°, GC purity: 98.3%.

A 10 liter four-necked sulphonation flask, equipped with a mechanical stirrer, thermometer and gas inlet arrangement, is charged under argon with 692 g (3.2 mol) of 2-butyl 5-chloropyridine-2-carboxylate and 7 l of ethylene diamine and the clear solution obtained is stirred, whereby the internal temperature rises slowly from 22° to a maximum of 30° during the stirring. The course of the reaction is followed by gas chromatography. After a reaction period of 3 hours (the internal temperature still amounts to 27°) the reaction solution is evaporated at 30°–40° under reduced pressure. The evaporation residue—a clear, yellow oil— weighs 753 g. A 20 liter stirring vessel as well as two 5 liter separating funnels are charged with, respectively, 2.250 l of ice-cold 3N hydrochloric acid, 750 ml of 1.5N hydrochloric acid and 750 ml of deionized water. The evaporation residue (753 g of a clear, yellow oil) is subsequently treated with 1.500 l of methylene chloride and the solution obtained is added to the stirring vessel. After intermixing of the two phases the pH value of the aqueous phase amounts to about 1. Subsequently, the organic phase from the stirring vessel as well as two 1.5 l portions of methylene chloride are passed in sequence and with good intermixing through the stirring vessel and the two separating funnels. The aqueous phases are combined in the stirring vessel and adjusted to about pH 11 by the addition of 3 l of ice-cold 3N sodium hydroxide solution. The two separating funnels are charged with two 750 ml portions of semi-saturated sodium chloride solution. Then, in each case with good intermixing, six 1.5 l portions of methylene chloride are passed through the stirring vessel and the two separating funnels. The organic phases are combined and dried over 500 g of sodium sulphate. The drying agent is filtered off and the filtrate is evaporated at 30°–40° under reduced pressure. The yellow, oily residue is dried at 40°/0.1 Pa for a further 15 hours and thereafter weighs 616 g (3.08 mol). It crystallizes upon standing at 20°. The crystallizate is dissolved in 3.2 l of methanol at 20°. 688 ml of 4.48N methanolic hydrochloric acid (3.08 mol) are added in one portion to the solution while cooling in an ice bath. The reaction mixture is stirred for 15 minutes and the resulting suspension is subsequently heated to 50°, whereby a clear solution again results. Thereto there are added within 30 minutes 5.8 l of t-butyl methyl ether (pre-heated to 50°). The suspension obtained is left to cool to 20° (duration about 1.5 hours) and it is subsequently cooled to 0°–5° with an ice bath. The solid is subsequently filtered off and rinsed with 1.100 l of petroleum ether (low-boiling). The crystallizate is subsequently dried to constant weight at 40° in a vacuum drying oven and thereafter weighs 693 g (95% crystallization yield). For further purification, the crystallizate is heated to 55° in 3.6 l of methanol and dissolved. While stirring vigorously there are allowed to drop in within 1.5 hours 5.500 l of t-butyl methyl ether (pre-heated to 50°), whereby the mixture is seeded with pure crystals of the end product after the addition of 1.5 l of solvent. The suspension obtained is left to cool to about 20° (duration about 1.5 hours), whereupon it is cooled to 0°–5° with an ice bath. The crystallizate is filtered off and washed with 1.1 l of pentane. The N-(2-aminoethyl)-5-chloropyridine-2-carboxamide hydrochloride obtained is dried in a high vacuum at 50°/1 Pa for two days and thereafter weighs 665 g (87%), m.p. 197°–199°.

EXAMPLE 13

9.0 ml (80 mmol) of 1-hexyne and 6.0 g (40 mmol) of 2,5-dichloropyridine in 80 ml of diethylamine are placed under argon, whereby a pale yellow solution results. Thereto there are added 0.40 g (1.5 mmol) of triphenylphosphine, 0.04 g (0.02 mmol) of copper-(I) iodide as well as 0.24 g (0.9 mmol) of palladium-dichloro-bis(triphenylphospine). The orange solution obtained is subsequently heated to reflux for 24 hours while stirring. Thereafter, the reaction mixture is cooled to 25° and evaporated at 40° under reduced pressure.

The brown residue is then treated with 50 ml of ethanol and again evaporated. The crude product is filtered over 50 g of silica gel with 700 ml of hexane/toluene (1:1) and the eluate is evaporated at 50° under reduced pressure. The residue is subsequently distilled in a bulb tube at 190°/2600 Pa. There are obtained 6.8 g of 2-hexynyl-5-chloropyridine as a yellow oil.

EXAMPLE 14

1.2 ml (10 mmol) of trimethylsilylacetylene, 40 ml of diethylamine and 1.5 g (10 mmol) of 2,5-dichloropyridine are stirred at 20° under argon. To the colourless solution obtained there are added 0.1 g (0.4 mmol) of triphenylphosphine, 0.01 g (0.05 mmol) of copper-(I) iodide as well as 0.06 g (0.25 mmol) of palladium-dichloro-bis(acetonitrile). The reaction solution is subsequently heated to reflux for 5 hours while stirring. After cooling to 25° the reaction solution is evaporated at 40° under reduced pressure. 50 ml of ethanol are subsequently added to the residue and the mixture is again evaporated. The crude product is filtered over 30 g of silica gel with ethyl acetate and the eluate is evaporated, whereby 1.6 g of brown liquid remain behind. 1.0 g thereof is distilled in a bulb tube at 70°/0.1 Pa, whereby there are obtained as the main fraction 0.6 g of 2-trimethylsilylethynyl-5-chloropyridine which solidifies upon standing.

0.10 g (0.5 mmol) of 2-trimethylsilylethynyl-5-chloropyridine, 0.01 g of sodium lauryl sulphate and 2 ml of deionized water are placed under an inert gas atmosphere. Subsequently, 0.25 g (15 mmol) of potassium permanganate is added thereto at 23° while stirring. After 2 hours the reaction mixture is treated with aqueous sodium bisulphite solution (about 40 percent) until, after filtration of a sample over filter paper, the violet colour of the permanganate has disappeared. The suspension is filtered over a layer of Dicalite and the filtrate is adjusted to pH 3 with 1N aqueous hydrochloric acid, whereby a white suspension results. This is cooled in an ice bath and the crystals are filtered off. The crystals are treated with 1 ml of deionized water, the suspension is again cooled to 0° and the crystals are filtered off. These are evaporated twice from methanol/toluene under reduced pressure and the residue is dried in a high vacuum. There are obtained 17 mg of 5-chloropyridine-2-carboxylic acid as a white, solid residue, m.p. 171°–172°.

EXAMPLE 15

The carbonylation of 5.0 g (33.8 mmol) of 2,5-dichloropyridine in 50 ml of methanol/triethylamine 1:1 in the presence of 0.47 g of palladium dichloro-bis(triphenylphosphine) at 110° is carried out in a manner analogous to Example 1. Working-up of the crude product as in Example i yields 2.86 g (49%) of crude methyl 5-chloropyridine-2-carboxylate which, by crystallization from hexane, yields pure methyl 5-chloropyridine-2-carboxylate in the form of white crystals, m.p. 83°–86°.

We claim:

1. A process for the preparation of pyridine-2-carboxamides of the formula

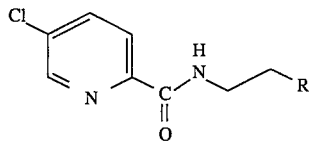

I wherein R is amino or a residue convertible into amino, which comprises reacting 2,5-dichloropyridine of the formula

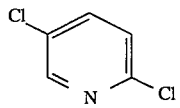

II in the presence of a palladium-phosphine catalyst wherein the palladium-phosphine catalyst is prepared in situ from 0.0001–0.05 mol % of metallic palladium or a complex or salt of 0-, 2- or 4-valent palladium and 0.01–100 mol per mol of palladium of a phosphorus compound of the formula

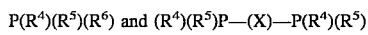

wherein $R^4$, $R^5$ and $R^6$ each independently are $C_{1-8}$-alkyl, cyclohexyl, benzyl, phenyl or phenyl which is substituted by $C_{1-4}$-alkyl, $C_{1-4}$-alkoxy, halogen, trifluoromethyl or phenyl and X is binaphthyl or one of the groups —$(CH_2)_n$—, $CH_2CH_2$—$P(C_6H_5)$—$CH_2$—$CH_2$—,

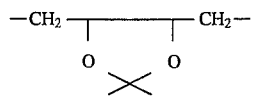

or

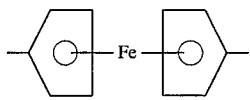

and n is 1–8 with carbon monoxide and an amino compound of the formula

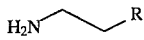

VI wherein R is as described above.

2. A process for the preparation of pyridine-2-carboxamides of the formula

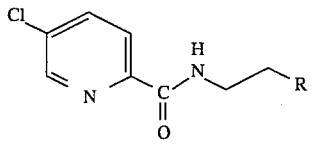

I wherein R is amino or a residue convertible into amino, which comprises reacting 2,5-dichloropyridine of the formula

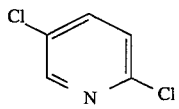

II in the presence of a palladium-phosphine catalyst with carbon monoxide and an amino compound of the formula

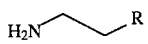

VI wherein R is as described above.

3. A process according to claim 2, wherein the reaction is carried out in the presence of a base.

4. A process according to claim 3, wherein the base is triethylamine.

5. A process according to claim 2, wherein the reaction is carried out in an aromatic hydrocarbon, an ether or a carboxylic acid ester.

6. A process according to claim 5, wherein the reaction is carried out in toluene, tetrahydrofuran or ethyl acetate.

7. A process according to claim 2, wherein the reaction is carried out at a temperature between about 60° and 150° C.

8. A process according to claim 7, wherein the reaction is carried out at a temperature between about 100° and 130° C.

9. A process according to claim 2, wherein the reaction is carried out at a pressure of about $10^5$ to about $10^7$ Pa.

10. A process according to claim 9, wherein the reaction is carried out at a pressure of about $10^6$ Pa.

11. A process according to claim 2, wherein the palladium-phosphine catalyst is prepared in situ.

12. A process according to claim 11, wherein the palladium-phosphine catalyst is prepared from 0.0001–0.5 mol % of metallic palladium or a complex or salt of O-, 2- or 4-valent palladium and 0.01–100 mol per mol of palladium of a phosphorus compound of the formulae $P(R^4)(R^5)(R^6)$ and $(R^4)(R^5)P$—$(X)$—$P(R^4)(R^5)$ wherein $R^4$, $R^5$ and $R^6$ each independently are $C_{1-8}$-alkyl, cyclohexyl, benzyl, phenyl or phenyl which is substituted by $C_{1-4}$-alkyl, $C_{1-4}$-alkoxy, halogen, trifluoromethyl or phenyl and X is binaphthyl or one of the groups —$(CH_2)_n$—, —$CH_2CH_2$—$P(C_6H_5)$—$CH_2$—$CH_2$—,

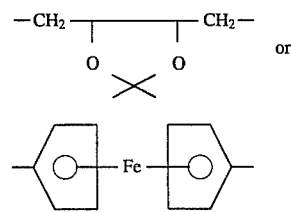

and n is a number of 1–8.

13. A process according to claim 12, wherein palladium-(II) chloride or palladium-(II) acetate and a bis(diphenylphosphino)alkane, is used for the preparation of the palladium-phosphine catalyst.

14. A process according to claim 13, wherein the bis-(diphenylphosphino)alkane is (diphenylphosphino)propane.

15. A process according to claim 12, wherein 0.01–0.1% of palladium component and 0.1–10 mol of phosphine ligand are used per mol of palladium.

16. A process according to claim 13, wherein 0.01–0.1% of palladium component and 0.1–10 mol of phosphine ligand are used per mol of palladium.

17. A process according to claim 2, wherein ethylenediamine or t-butyl(2-aminoethyl)carbamate is used as the amino compound of formula VI.

18. A process for the preparation of pyridine-2-carboxamides of the formula

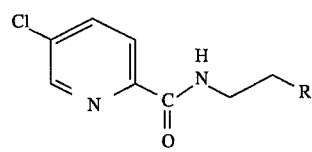

wherein R is amino or a residue convertible into amino, which comprises reacting 2,5-dichloropyridine of the formula

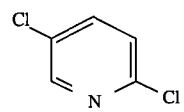

in the presence of a palladium-phosphine catalyst with carbon monoxide and a lower alkanol optionally mixed with water to give 5-chloropyridine-2-carboxylic acid of the formula

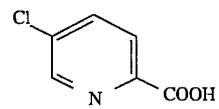

or a lower alkyl ester thereof and reacting the resulting acid or the resulting lower alkyl ester or another reactive functional derivative of this acid with an amino compound of the formula

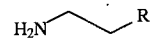

wherein R is as described above.

19. A process according to claim 2, wherein R is a residue convertible into amino which further comprises converting said residue into amino.

20. A process according to claim 2 or 19 which further comprises converting the compound of formula I wherein R is amino into a pharmaceutically usable acid addition salt.

* * * * *